United States Patent [19]

Katayama et al.

[11] Patent Number: 5,291,886
[45] Date of Patent: Mar. 8, 1994

[54] APPARATUS FOR MEASURING BLOOD FLOW

[75] Inventors: Koji Katayama; Ayafumi Taniji; Muneharu Ishikawa, all of Tsukuba, Japan

[73] Assignee: Kowa Company Ltd., Japan

[21] Appl. No.: 795,848

[22] Filed: Nov. 21, 1991

[30] Foreign Application Priority Data

Nov. 27, 1990 [JP] Japan .................. 2-320641

[51] Int. Cl.⁵ .............................................. A61B 5/00
[52] U.S. Cl. ..................................... 128/633; 128/634
[58] Field of Search .................................. 128/633, 634

[56] References Cited

U.S. PATENT DOCUMENTS

| | | | |
|---|---|---|---|
| 4,542,657 | 9/1985 | Barber et al. | 128/661.09 |
| 4,817,627 | 4/1989 | Cohen et al. | 128/731 |
| 4,862,894 | 9/1989 | Fujii | 128/666 |
| 4,869,254 | 9/1989 | Stone et al. | 128/633 |
| 4,934,372 | 6/1990 | Corenman et al. | 128/666 |
| 5,115,137 | 5/1992 | Andersson-Engels et al. | 128/633 |
| 5,135,000 | 8/1992 | Akselrod et al. | 128/662.02 |
| 5,146,091 | 9/1992 | Knudson | 128/633 |

*Primary Examiner*—Randall L. Green
*Assistant Examiner*—Gina M. Gualtieri
*Attorney, Agent, or Firm*—Bruce L. Adams; Van C. Wilks

[57] ABSTRACT

An apparatus for measuring blood flow repeatedly segmentally scans a region of in vivo tissue with a coherent light beam. Each scanning segment comprises a scanning period during which the light beam is scanned and a rest period during which the light beam is not scanned. During the rest period, the light beam is directed at a measuring point of the in vivo tissue. Measurement data is obtained dependent on the intensity of scattered light from the measurement point. The measurement data is time series data of chronological changes in the intensity of scattered light caused by blood in the in vivo tissue. The blood flow rate is calculated from frequency-analysis of the time series data.

19 Claims, 5 Drawing Sheets

APPARATUS FOR MEASURING BLOOD FLOW

BACKGROUND OF THE INVENTION

The present invention relates to an apparatus for measuring blood flow, and more particularly to an apparatus for measuring blood flow for noninvasively obtaining blood flow information.

Apparatuses employing laser beam irradiation for noninvasively measuring data relating to blood flow within in vivo tissue are well known. Most of these prior art apparatuses project a laser beam onto the in vivo tissue so as to obtain a speckle pattern by interference among the rays of light scattered by corpuscles within the tissue. The speckle pattern varies with the movement of the corpuscles and it is possible to obtain a speckle signal proportional to the corpuscle velocity by, for example, measuring the variation in intensity of the light reflected from a single point. Thus in apparatuses of this type, data relating to blood flow is obtained from variations in the speckle signal.

In one such prior art method of obtaining blood flow data, the measurement is carried out by using optical fiber probes for detecting time-course variation in the intensity of light reflected at selected measurement points. This method is directed solely to obtaining data in respect of a single point and, therefore, does not allow observation of blood flow distribution over a given area.

There is also known a method of measuring blood flow distribution by two-dimensionally scanning the in vivo tissue with a laser beam. This method is described in Japanese, Patent; Public Disclosure Sho 63(1988)-214238 which discloses using a mirror to scan the in vivo tissue surface with a laser beam spot that has been linearly expanded by a cylindrical lens. The reflected scattered light is detected with an image sensor. Also, this method is described in Japanese Patent Public Disclosure Sho 64(1989)-37931 which discloses using a light deflecting element for reciprocally scanning the in vivo tissue surface with a light spot at a prescribed, scanning period. Blood flow data is derived from the difference between two light signals obtained from the same spot at two points of time separated by a prescribed time interval.

Since these prior art measurement methods require continuous scanning involving the reciprocal movement of irradiating light with respect to the in vivo tissue surface, a prerequisite of their use is that the in vivo tissue under examination be maintained stationary throughout the measurement. Specifically, since the data is compared and calculated at every measurement point within the measurement region during every scanning cycle, any shift in the measurement points would affect all of the measurement data and immediately deprive it of reliability.

Moreover, while the two-dimensional scanning enables spatially continuous measurement, it is intermittent in terms of time from the viewpoint of any given single scanned point. As a result, the frequency of the speckle signal obtained is dependent on the scanning frequency. Where measurement is conducted with respect to rapid blood flow such as encountered in the eye fundus, for example, the speckle signal falls in a high frequency band and, with the conventional methods, it becomes necessary to increase the scanning speed accordingly. This makes it necessary to use a more complex apparatus.

SUMMARY OF THE INVENTION

An object of the present invention is therefore to provide an apparatus capable of handling high-frequency speckle frequencies arising as a result of high blood flow velocity such as observed in the eye fundus. Another object of the present invention is to provide an apparatus capable of measuring blood flow distribution within a two-dimensional spatial plane, and outputting the results of the measurement in an easily understandable form.

In accordance with the present invention, the above object is achieved by an apparatus for measuring blood flow comprising intermittent scanning means for repeatedly carrying out segmental scans. Each scan consists of a period during which a segment of a prescribed two-dimensional plane of an in vivo tissue is spatially scanned with coherent light and a rest period. Means are provided for measuring time series data relating to the intensity of scattered light from the in vivo membrane during the rest period of each segmental scan. Data relating to blood within the in vivo tissue is calculated from time series data relating to the scattered light intensity measured by the measurement means. According to another aspect of the invention, the apparatus for measuring blood flow is further provided with means for two-dimensionally displaying the data obtained during every rest period based on the measurement conducted by the spatially intermittent two-dimensional scanning with the coherent light. According to still another aspect of the invention, the apparatus for measuring blood flow is further provided with imaging means for picking up an image of the region two-dimensionally scanned with the coherent light. Also, means for analyzing positional displacement data obtained from the image picked up by the imaging means is provided. The measurement data obtained for the measurement points by the spatially intermittent two-dimensional scanning with the coherent light is corrected by correcting means so as to compensate for any positional displacement of the measurement points. The corrected measurement data is displayed and the image of the scanned region is superimposed on each other by displaying means.

Thus, since the apparatus for measuring blood flow according to the invention intermittently scans the two-dimensional plane in segmental scans each comprised of a scanning period and a rest period, the frequency range with respect to which measurement can be conducted during each rest period is not dependent on the scanning frequency. This makes it possible to conduct measurement in the high frequency range.

As the aforesaid intermittent scanning enables the measurement at the each measurement point to be completed before the next segmental scan begins, the tissue under examination does not have to remain still throughout the entire measurement period and it suffices for it to be kept immobile during the rest period. Moreover, even if it should move during the measurement period, the motion will, at most, affect only one or two measurement points, and the other measurement data, particularly that with respect to points for which measurement has been completed, will be unaffected.

In such cases, however, a distorted two-dimensional distribution differing from the intended one will arise between the measurement results for the points measured before the tissue movement and the measurement results for the points measured after the tissue movement. Correction for this distortion is therefore carried out by storing a visible image in an image memory synchronously with the entire scanning period and then, after the measurement has been completed, using the stored image to correct for measurement point displacement and thereby obtaining the intended two-dimensional distribution.

The measurement data obtained can thus be two-dimensionally displayed and, moreover, the measured blood flow data can be displayed as superimposed on an image of the measurement region.

Furthermore, the measurement is conducted independently at each measurement point and, therefore, an accurate measurement value can be obtained at each point irrespective of any movement of the tissue under examination.

BRIEF DESCRIPTION OF THE DRAWINGS

The purposes and features of the present invention will become more apparent from a consideration of the following detailed description taken in conjunction with the accompanying drawings in which.

DETAILED DESCRIPTION OF THE PREFERRED EMBODIMENT

Figure 1:
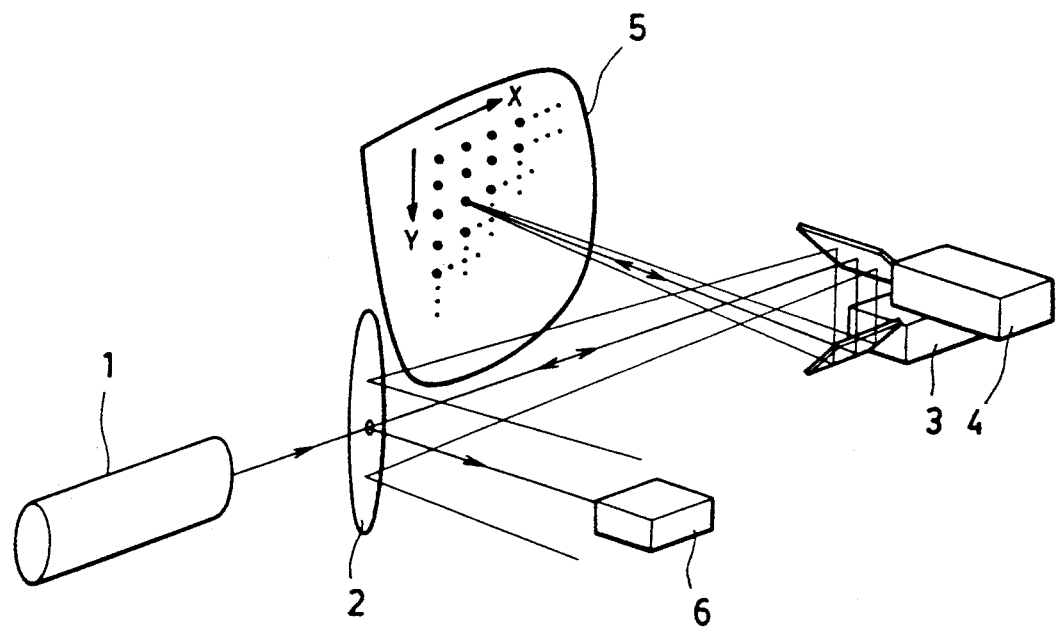
FIG. 1 is a perspective schematic view of the measurement optical system of an apparatus for measuring blood flow incorporating the present invention.

The invention will now be described in detail on the basis of the preferred embodiment illustrated in the drawings.

The perspective view of the measurement optical system of an apparatus for measuring blood flow incorporating the present invention shown in FIG. 1 has been simplified by the omission of a CCD (charge-coupled device) camera image pick-up optical system that will be explained later.

A laser beam emitted by a laser beam source 1 passes through the center hole of a perforated mirror 2 and is reflected onto an in vivo tissue (measurement region) 5 by galvanoscanners 3 and 4 arranged to deflect the beam in mutually perpendicular directions. The galvanoscanners 3 and 4 are controlled by analog drivers for deflecting the beam along the Y axis and the X axis, respectively.

The scattered light reflected from the vicinity of the laser beam spot on the in vivo tissue 5 is reflected by the galvanoscanners 3 and 4 and then by the peripheral region of the perforated mirror 2 toward a light receiving section 6.

Figure 2:
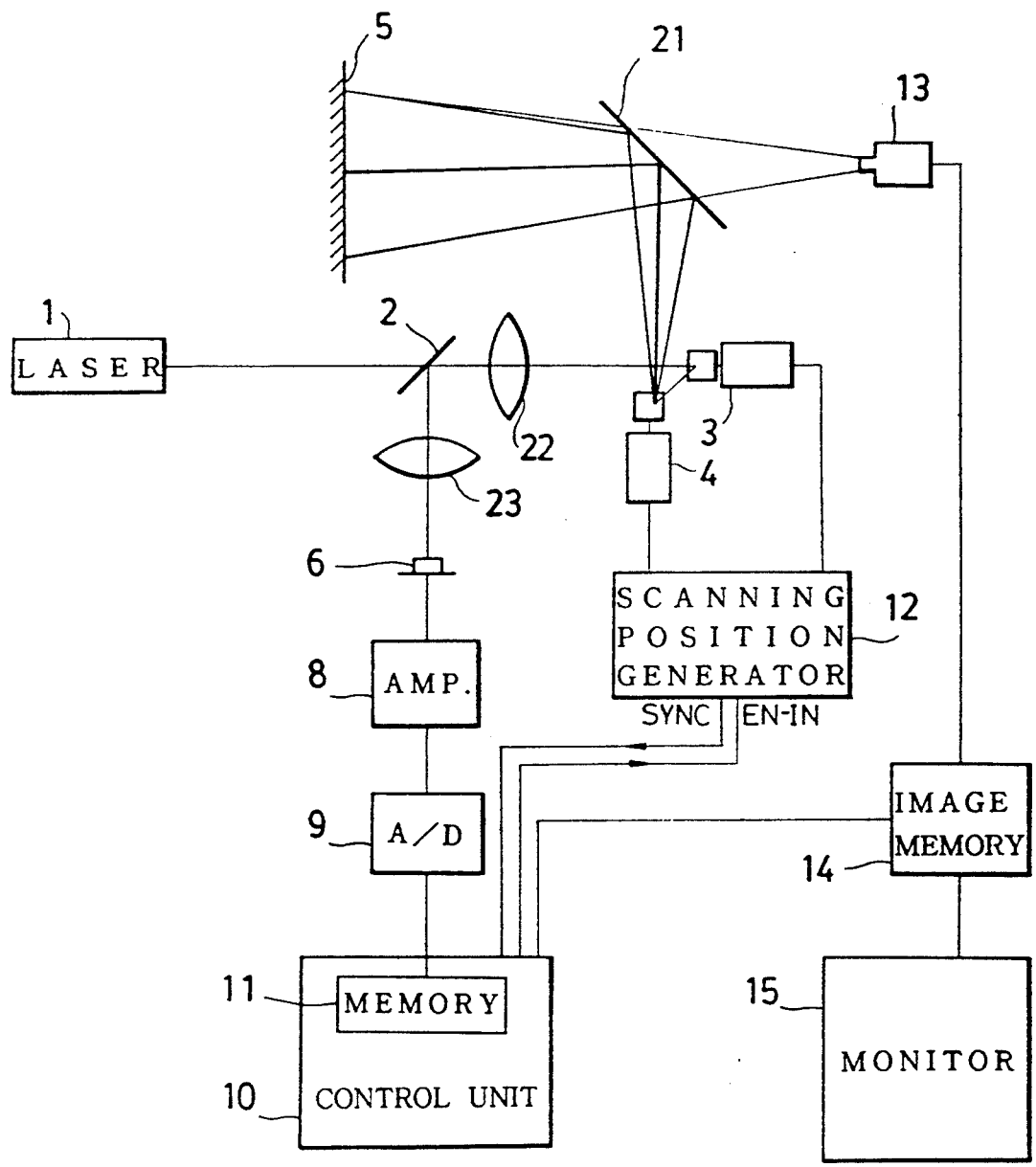
FIG. 2 is a block diagram showing the measurement optical system, the control system and the image pick-up system of the apparatus for measuring blood flow of FIG. 1.

The overall arrangement of the apparatus for measuring blood flow including the aforesaid optical system and the measurement and control systems is shown in FIG. 2.

The output of the light receiving section 6 is amplified by an amplifier 8 and then fed to an A/D converter 9 for conversion into a digital signal for storage in a memory 11 of a control unit 10, which can be a personal computer or the like.

The control unit 10, which serves as the control system for the apparatus for measuring blood flow as a whole, controls the measurement spot by controlling the angles of the galvanoscanners 3 and 4 via a scanning position generator 12.

Figure 3:
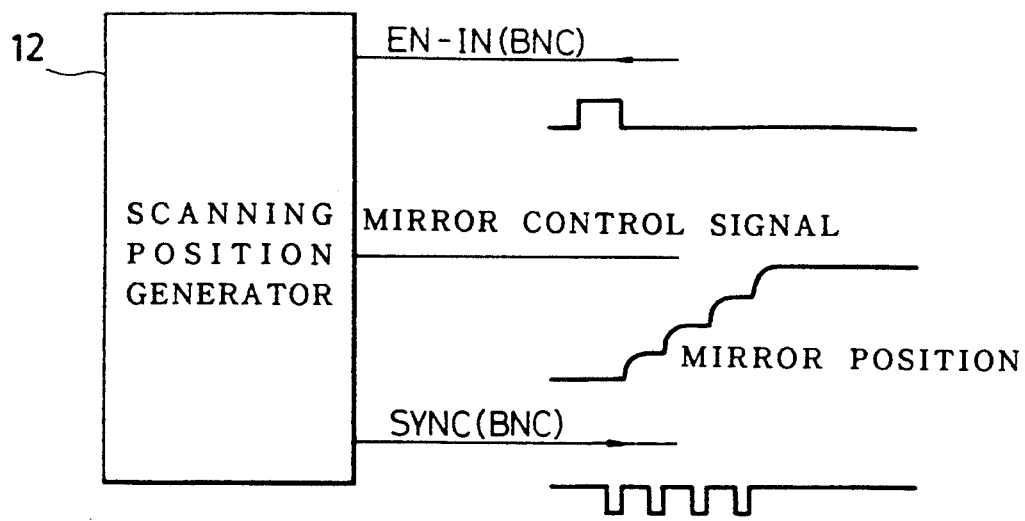
FIG. 3 is a diagram for explaining the structure and operation of the scanning position generator shown in FIG. 2.

As shown in FIG. 3, the scanning position generator 12 receives a mirror control signal and an EN-IN signal for triggering one set of segmental scan operations and outputs to the control unit 10 a SYNC signal constituting a timing clock signal synchronized with the movement of the galvanoscanners 3 and 4.

Based on these control signals, the scanning position generator 12 controls the galvanoscanners 3 and 4 for positioning the laser beam spot at prescribed measurement points on the in vivo tissue 5. In this particular embodiment, a total of 16×16 (=256) measurement points are formed on the measurement region of the vivo tissue 5.

Returning to FIG. 2, light scattered from the measurement region 5 passes through a dichromic mirror 21 disposed in the measurement optical system and is received by a CCD camera 13 for imaging the measurement plane. While the positioning of the laser spot with respect to the measurement region 5 is being conducted, the measurement optical system, the dichromic mirror 21 and the CCD camera 13 shown in FIG. 2 are maintained in a prescribed positional relationship by a coordinating mechanism (not shown).

The picture imaged by the CCD camera 13 is stored in an image memory 14 as picture data for display on a monitor 15. In the present embodiment, the control unit 10 operates via the image memory 14 to display a desired image on the monitor 15 and the image data from the CCD camera 13 is displayed as superimposed thereon.

The operation of the apparatus for measuring blood flow of the foregoing arrangement will now be explained.

Measurement is started by pressing a prescribed key on the keyboard (not shown) of the control unit 10. When the prescribed key is pressed, the control unit 10 outputs the EN-IN signal announcing the start of measurement, whereby mirror scanning is begun. The scanning position generator 12 outputs the mirror control signal designating the deflection angle of the mirrors so as to control the position of the laser with respect to both the X and Y axes. It also outputs a clock signal synchronized with the movement of the mirrors to the control unit 10.

Thus the galvanoscanner 3 (or 4, depending on how the X and Y axes are defined) is controlled to progressively move the laser spot along the Y axis. As the laser beam spot moves from measurement point to measurement point, the scattered light reflected from each point is received by the light receiving section 6 and then converted to a digital value which is stored in the memory 11.

When the scanning of one line has been completed, the galvanoscanner 4 (or 3, depending on how the X and Y axes are defined) for moving the laser beam spot along the X axis moves the laser spot to the next measurement line, where similar measurement is conducted. The procedure just described is carried out repeatedly until measurement has been conducted for all of the measurement points.

Measurement data is thus obtained for a finite number of measurement points within the measurement region. In the particular measurement example at hand, the intensities of the scattered light from 256 (16×16) measurement points are stored in the memory 11.

Figure 4:
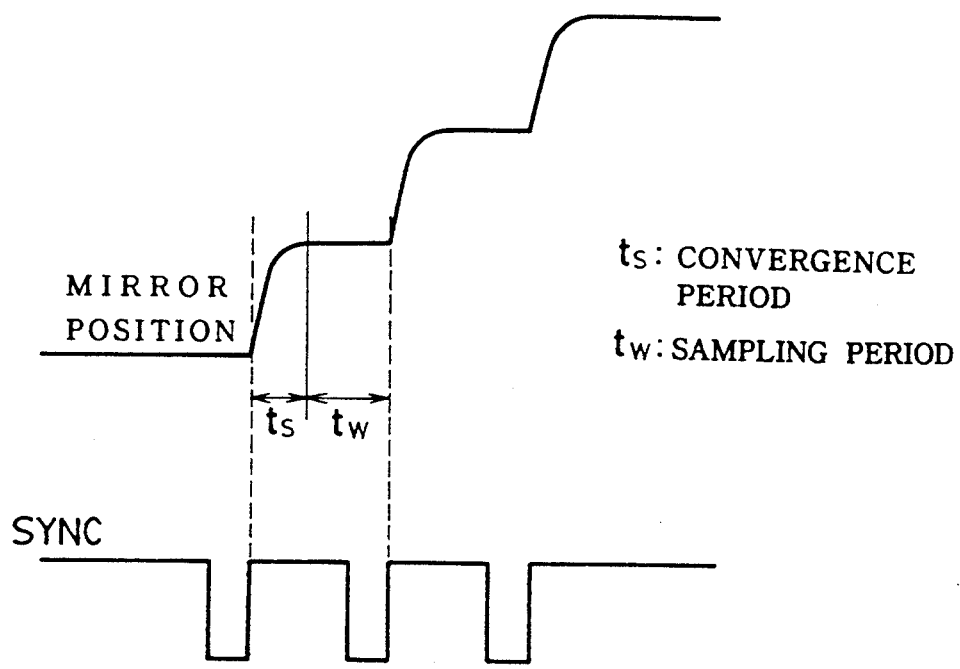
FIG. 4 is a timing chart showing the synchronization between the control of the mirror position (angle) by the scanning position generator and a clock signal output to the control unit.

FIG. 4 shows how the position (angle) of the galvanoscanners 3 and 4 and the SYNC signal are synchronized. In the case of the galvanoscanners used in tests it was found that once mirror movement had begun the time tS (the convergence period) required for it to reach a still state enabling measurement was 4 ms. Sampling of the amount of light received by the light receiving section 6 was carried out during sampling period tW (approx. 2.6 ms) following the convergence period.

Where the sampling is conducted at 5 µs intervals using a 12-bit A/D board installed in a personal computer as the A/D converter 9 and 512 samples are taken for each measurement point, the time required for measurement at each point is 1.68 s. The frequency range over which measurement is possible under these conditions is from about 400 Hz to about 100 KHz. The arrangement described in the foregoing thus makes it possible to measure spectral signal in the high frequency range and, moreover, enables the measurement to be completed in a single scan.

Thus, since the galvanoscanners 3 and 4 intermittently scan the two-dimensional plane in segmental scans each comprised of a scanning period and a rest period, the frequency range with respect to which measurement can be conducted during each rest period (for each measurement point) is not dependent on the scanning frequency. Measurement can thus be conducted at higher frequencies than has been possible in the past and, moreover, can be adapted as required by differences in blood flow velocity between different parts of the measurement region.

Upon completion of measurement, the intensity data relating to the light received from the respective measurement points is analyzed for obtaining blood flow data. For example, frequency analysis is conducted with respect to the individual measurement points and the blood flow velocity distribution data obtained in this way is displayed on the monitor 15 by mapping of variable density (or color) dots. It is thus possible to measure blood flow distribution within a two-dimensional plane simply and noninvasively, while at the same time displaying the results of the measurement two-dimensionally.

Figure 5A:
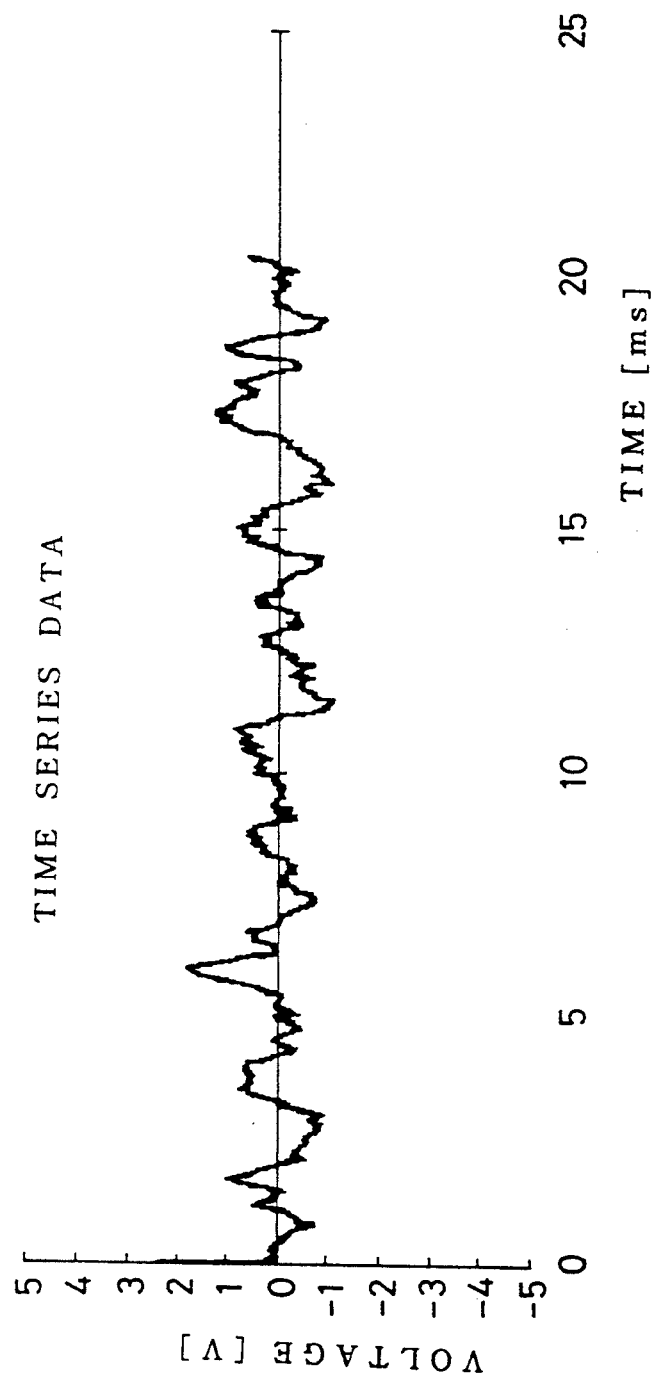
FIGS. 5a and 5b are graphs showing an example of actually measured time series data and the frequency data obtained by frequency analysis of the time series data.
Figure 5:
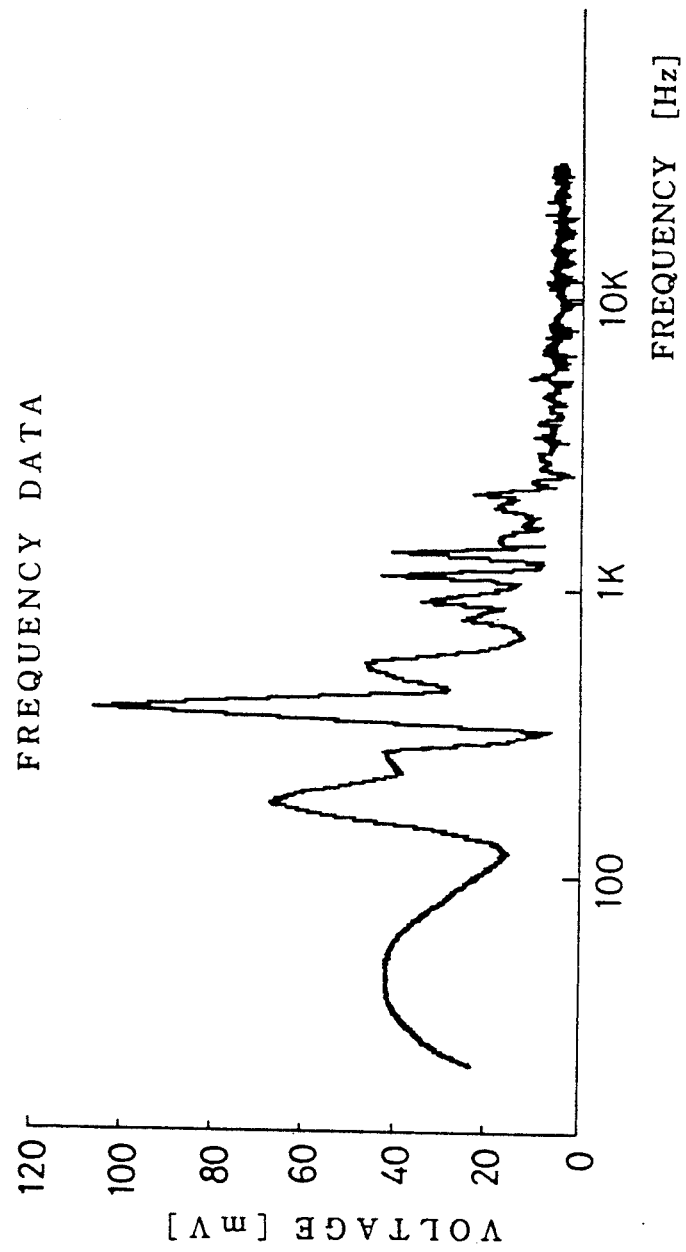

FIG. 5a shows the AC component of light quantity variation at the light receiving section 6 in the form of time series data, while FIG. 5b shows an example of frequency data obtained by frequency analysis of the AC component. Blood flow velocity data can be derived from this frequency data. The control unit 10 may include calculating means for calculating data from the time series data so that the time series data is frequency-analyzed and blood-flow information is calculated dependent on a frequency spectrum derived from the frequency-analyzation.

In another arrangement according to the invention a frequency component corresponding to the blood flow is extracted by amplifying the signals for the individual measurement points and then passing them through an analog frequency filter, whereby the data relating to the measurement points can be obtained in real time. It is also possible to install a frequency filter and an analog operating circuit in the amplifier 8 shown in FIG. 2. In this case data representing the results of analysis is supplied directly to the A/D converter 9 and is thereafter processed in the control unit 10.

The analog operating circuit is controlled by a scanning position signal from the control unit 10 so as to shut out signals produced during scanning, which are unnecessary for the analysis, and ensure that only signals arising during the rest periods will processed by the frequency filter and the operating circuit.

Further, the image memory 14 can be controlled so as to display the mapped information as superimposed on the picture of the measurement region produced by the CCD camera 13. The superimposition of the picture data can be conducted by the CPU of the control unit 10 using a known method employing OR or XOR processing with respect to the individual dots of the bit map for the monitor 15 in the image memory 14.

This superimposed display of the blood flow data obtained by laser beam scanning and the picture obtained by the CCD camera 13 makes it easier for the operator to visually grasp the measurement data.

Attachment of a marker to the in vivo tissue under examination before the start of measurement enables movement of the tissue to be readily discerned from movement of the image of the marker within the picture of the measurement region and, therefore, facilitates the task of correcting the positional data part of the measurement data obtained by the intermittent scanning. Specifically, if the tissue should move at a given time during the scanning for measurement, the presence of the marker makes it easy to obtain positional information regarding the measurement points after the movement from the picture of the measurement region and thus facilitates the correction for the movement. It is further possible to use an arrangement in which the superimposition of the picture and measurement data is carried out on the basis of the corrected positional information. On the other hand, if the tissue should move during a rest period, i.e. while measurement is in progress, a warning indication can be affixed to the measurement data concerned and displayed together therewith.

In the embodiment described in the foregoing, the control conditions of the galvanoscanners 3 and 4 can be changed for varying the scanning range to match the size of the desired measurement region. Since this embodiment uses a personal computer as the control unit 10, the measurement range can be easily set to the size desired by appropriate programming changes or by running a program designed for changing the control conditions.

It should also be noted that a printer can be added to the system described in the foregoing for the purpose of producing hard copies of the picture data stored in the image memory 14 for display on the monitor 15.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An apparatus for measuring blood flow comprising:
   intermittent scanning means for repeatedly carrying out segmental scans each consisting of a period during which a segment of a prescribed two-dimensional plane of an in vivo tissue is spatially scanned with coherent light and a rest period during which coherent light is directed at a measurement point of the in vivo tissue;
   measuring means for, during the rest period of each segmental scan, measuring time series data relating to intensity of scattered light from the measurement point in the in vivo tissue; and
   calculating means for calculating data relating to blood within the in vivo tissue from the time series data by frequency analyzing the time series data and calculating blood-flow information dependent on a frequency spectrum derived from the frequency-analyzation.

2. An apparatus according to claim 1, further comprising a control unit for removing unneeded signals occurring during the course of scanning before the calculation is performed.

3. An apparatus according to claim 1, further comprising displaying means for two-dimensionally displaying the data obtained by the measuring means.

4. An apparatus according to claim 1, further comprising imaging means for picking up an image of a region two-dimensionally scanned with the coherent light, correcting means for analyzing positional displacement data obtained from the image picked up by the imaging means and correcting the measurement data obtained for the measurement points so as to compensate for any positional displacement of the measurement points, and displaying means for displaying the corrected measurement data and the image of the scanned region as superimposed on each other.

5. An apparatus for measuring blood flow, comprising: scanning means for segmentally scanning in vivo tissue with a light beam, each scanning segment comprising a scanning period during which the in vivo tissue is scanned with the light beam, and a rest period during which the in vivo tissue is not scanned and the light beam is directed at a measurement point of the in vivo tissue; and measuring means for measuring measurement data derived from intensity fluctuations of a speckle pattern obtained from the measurement point during the rest period.

6. An apparatus for measuring blood flow according to claim 5 further comprising calculating means for calculating blood flow information dependent on the measurement data.

7. An apparatus for measuring blood flow according to claim 6 wherein the measurement data is time series data; and wherein the calculating means includes means for calculating the blood flow information based on the frequency of the time series data.

8. An apparatus for measuring blood flow according to claim 6 further comprising controlling means for controlling the calculating means to calculate blood flow information only from measurement data obtained during the rest period.

9. An apparatus for measuring blood flow according to claim 8 wherein the controlling means includes means for preventing the calculating means from receiving data obtained during the scanning period.

10. An apparatus for measuring blood flow according to claim 5 further comprising displaying means for displaying an image dependent on the measurement data.

11. An apparatus for measuring blood flow according to claim 5 further comprising imaging means for receiving an image of a region of the in vivo tissue being segmentally scanned; and correcting means for analyzing positional displacement data of the measuring point from the image and correcting the measurement data so as to compensate for any positional displacement and producing corrected measurement data.

12. An apparatus for measuring blood flow according to claim 11 further comprising displaying means for displaying an image derived from the corrected measurement data in superposition with an image of the region of in vivo tissue.

13. An apparatus for measuring blood flow according to claim 5 wherein the scanning means includes means for scanning with a coherent light beam.

14. An apparatus for measuring blood flow, comprising: scanning means for repeated segmental scanning of a region of in vivo tissue with a coherent light beam, each scanning segment comprising a scanning period during which the in vivo tissue is scanned with the light beam, and a rest period during which the in vivo tissue is not scanned and the light beam is directed at a measurement point of the in vivo tissue; measuring means for measuring measurement data dependent on the intensity of scattered light from the measurement point, the measurement data being time series data of chronological changes in the intensity of scattered light caused by particles in blood in the in vivo tissue; and calculating means for calculating the flow rate of blood in the in vivo tissue from frequency analysis of the time series data.

15. An apparatus for measuring blood flow according to claim 14 wherein the calculating means includes means for calculating the blood flow rate dependent on a frequency spectrum of the time series data.

16. An apparatus for measuring blood flow according to claim 14 further comprising controlling means for controlling the calculating means to calculate the blood flow rate only from measurement data obtained during the rest period by preventing the calculating means from processing data obtained during the scanning period.

17. An apparatus for measuring blood flow according to claim 14 further comprising displaying means for displaying an image dependent on the measurement data.

18. An apparatus for measuring blood flow according to claim 14 further comprising imaging means for receiving an image of the region of the in vivo tissue being segmentally scanned; and correcting means for analyzing positional displacement data of the measuring point from the image and correcting the measurement data so as to compensate for any positional displacement and producing corrected measurement data.

19. An apparatus for measuring blood flow according to claim 18 further comprising displaying means for displaying an image derived from the corrected measurement data in superposition with an image of the region of in vivo tissue.

* * * * *